United States Patent
Silver

(10) Patent No.: US 11,147,934 B2
(45) Date of Patent: Oct. 19, 2021

(54) SYSTEM AND METHOD FOR LAUNCHING USAGE MODE IN A MULTIMODAL SURGICAL GAS DELIVERY SYSTEM

(71) Applicant: Conmed Corporation, Utica, NY (US)

(72) Inventor: Mikiya Silver, New Haven, CT (US)

(73) Assignee: Conmed Corporation, Utica, NY (US)

( * ) Notice: Subject to any disclaimer, the term of this patent is extended or adjusted under 35 U.S.C. 154(b) by 343 days.

(21) Appl. No.: 15/947,083

(22) Filed: Apr. 6, 2018

(65) Prior Publication Data

US 2018/0221597 A1 Aug. 9, 2018

Related U.S. Application Data

(60) Continuation-in-part of application No. 15/812,649, filed on Nov. 14, 2017, now Pat. No. 11,033,299, and
(Continued)

(51) Int. Cl.
*A61M 13/00* (2006.01)
*A61M 1/00* (2006.01)
(Continued)

(52) U.S. Cl.
CPC ....... *A61M 13/003* (2013.01); *A61B 17/3421* (2013.01); *A61B 17/3474* (2013.01);
(Continued)

(58) Field of Classification Search
CPC ............ A61M 13/003; A61M 2205/33; A61M 2205/75; A61M 2205/70; A61M 1/0031;
(Continued)

(56) References Cited

U.S. PATENT DOCUMENTS 4,735,603 A 4/1988 Goodson et al.
7,182,752 B2 2/2007 Stubbs et al.
(Continued)

FOREIGN PATENT DOCUMENTS

DE 4219859 A1 12/1993
EP 2482869 A1 8/2012
(Continued)

OTHER PUBLICATIONS

International Search Report and Written Opinion issued in corresponding PCT Patent Application No. PCT/US2019/025340, dated Jul. 18, 2019.
(Continued)

*Primary Examiner* — Lauren P Farrar
*Assistant Examiner* — Hamza A Darb
(74) *Attorney, Agent, or Firm* — Locke Lord LLP; Scott D. Wofsy; Joshua L. Jones

(57) ABSTRACT

A surgical gas delivery device includes a filter cartridge interface and a computer controlled control unit configured to control the circulation of surgical gas during endoscopic surgery. The control unit can operate in a plurality of different modes of operation. A tube set for connecting the surgical gas delivery device to one or more end effectors includes a filter cartridge in fluid communication with the tube set. The filter cartridge is seated in the filter cartridge interface of the surgical gas delivery device to communicate surgical gas between the surgical gas delivery device and the one or more end effectors. The surgical gas delivery device includes a reader operatively connected to receive input from a data carrying element of the tube set. The data carrying element, reader, and control unit can launch a specific one of the modes of operation when the filter cartridge is inserted.

13 Claims, 8 Drawing Sheets

Related U.S. Application Data a continuation-in-part of application No. 14/674,835, filed on Mar. 31, 2015, now Pat. No. 9,950,127, which is a division of application No. 13/862,851, filed on Apr. 15, 2013, now Pat. No. 9,067,030, which is a continuation of application No. 13/237,628, filed on Sep. 20, 2011, now Pat. No. 9,375,539.

(60) Provisional application No. 62/421,480, filed on Nov. 14, 2016, provisional application No. 61/384,412, filed on Sep. 20, 2010.

(51) Int. Cl.
| | | |
|---|---|---|
| *A61B 90/00* | (2016.01) | |
| *A61B 90/98* | (2016.01) | |
| *B01D 46/00* | (2006.01) | |
| *B01D 46/42* | (2006.01) | |
| *A61B 17/34* | (2006.01) | |
| *A61B 90/96* | (2016.01) | |
| *A61B 34/00* | (2016.01) | |
| *A61B 17/00* | (2006.01) | |

(52) U.S. Cl.
CPC .............. *A61B 34/25* (2016.02); *A61B 90/96* (2016.02); *A61B 90/98* (2016.02); *A61M 1/74* (2021.05); *A61M 13/00* (2013.01); *A61M 13/006* (2014.02); *B01D 46/0008* (2013.01); *B01D 46/4254* (2013.01); *A61B 2017/00199* (2013.01); *A61B 2017/00221* (2013.01); *A61B 2017/00225* (2013.01); *A61B 2090/064* (2016.02); *A61B 2090/0803* (2016.02); *A61B 2218/008* (2013.01); *A61M 2205/273* (2013.01); *A61M 2205/33* (2013.01); *A61M 2205/3344* (2013.01); *A61M 2205/505* (2013.01); *A61M 2205/6018* (2013.01); *A61M 2205/6054* (2013.01); *A61M 2205/6063* (2013.01); *A61M 2205/70* (2013.01); *A61M 2205/75* (2013.01); *A61M 2205/7509* (2013.01); *A61M 2205/7518* (2013.01); *B01D 46/429* (2013.01)

(58) Field of Classification Search
CPC ................ A61M 13/006; A61M 13/00; A61M 2205/273; A61M 2205/505; A61M 2205/6054; A61M 2205/6018; A61M 2205/3344; A61M 2205/6063; A61M 1/74; A61M 2205/7518; A61M 2205/7509; A61B 90/96; A61B 34/25; A61B 17/3474; A61B 2017/00199; A61B 2090/0803; A61B 2090/064; A61B 2218/008; A61B 2017/00221; A61B 90/98; A61B 17/3421; A61B 2017/00225; B01D 46/429; B01D 46/0008

See application file for complete search history.

(56) References Cited

U.S. PATENT DOCUMENTS

| | | | |
|---|---|---|---|
| 7,250,035 | B1 | 7/2007 | Ott et al. |
| 7,285,112 | B2 | 10/2007 | Stubbs et al. |
| 7,338,473 | B2 | 3/2008 | Campbell et al. |
| 7,413,559 | B2 | 8/2008 | Stubbs et al. |
| 7,854,724 | B2 | 12/2010 | Stearns et al. |
| 7,892,337 | B2 * | 2/2011 | Palmerton .............. A61B 18/00 96/424 |
| 2005/0140759 | A1 | 6/2005 | Hilton et al. |
| 2007/0088275 | A1 | 4/2007 | Stearns et al. |
| 2007/0249990 | A1 | 10/2007 | Cosmescu |
| 2009/0288561 | A1 | 11/2009 | Palmerton et al. |
| 2010/0185139 | A1 | 7/2010 | Stearns et al. |
| 2013/0231606 | A1 * | 9/2013 | Stearns .............. B01D 46/0008 604/26 |
| 2015/0112246 | A1 * | 4/2015 | Palmerton ........... A61M 13/003 604/26 |
| 2017/0028159 | A1 | 2/2017 | Ghalib et al. |
| 2017/0274160 | A1 | 9/2017 | Mantell et al. |

FOREIGN PATENT DOCUMENTS

| | | |
|---|---|---|
| JP | 2005-287840 A | 10/2005 |
| WO | 20100042204 A2 | 4/2010 |
| WO | 201141387 A1 | 4/2011 |

OTHER PUBLICATIONS

Supplemental Search Report dated Sep. 8, 2014 in connection with EP Application No. 11827365.

Office Action for Japanese Patent Application No. JP2013-529418, dated Jun. 23, 2015.

* cited by examiner

SYSTEM AND METHOD FOR LAUNCHING USAGE MODE IN A MULTIMODAL SURGICAL GAS DELIVERY SYSTEM

CROSS-REFERENCE TO RELATED APPLICATIONS

This application is a continuation in part of U.S. patent application Ser. No. 14/674,835 filed Mar. 31, 2015, which is a divisional of U.S. patent application Ser. No. 13/862,851 filed Apr. 15, 2013 (now U.S. Pat. No. 9,067,030), which in turn is a continuation of U.S. patent application Ser. No. 13/237,628 filed Sep. 20, 2011 (now U.S. Pat. No. 9,375,539), which in turn claims priority to U.S. Provisional Patent Application No. 61/384,412 filed Sep. 20, 2010. This application is also a continuation in part of U.S. patent application Ser. No. 15/812,649 filed Nov. 14, 2017, which claims priority to U.S. Provisional Application No. 62/421,480, filed Nov. 14, 2016. Each of these previously filed applications is incorporated by reference herein in its entirety.

BACKGROUND OF THE INVENTION

1. Field of the Invention

The subject invention is directed to endoscopic surgery, and more particularly, to a filter interface for a multimodal insufflation system used during endoscopic and/or laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such techniques include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum and allow the surgeon ample space to operate.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art. Such insufflation and smoke evacuation systems can be used for endoscopic procedures for a variety of different types of surgical cavities.

Additionally, SurgiQuest, Inc., Milford, Conn. USA, a wholly owned subsidiary of ConMed Corporation, has developed surgical access devices that permit access to an insufflated surgical cavity without conventional mechanical seals, and has developed related systems for providing sufficient pressure and flow rates to such access devices, as described in whole or in part in U.S. Pat. No. 7,854,724.

The present invention relates to multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids, such as with the above-mentioned surgical access devices described in U.S. Pat. No. 7,854,724, as well as those in U.S. Pat. Nos. 7,182,752, 7,285,112, 7,413,559 or 7,338,473. for example.

Use of a single multimodal system such as those described herein reduces costs by requiring purchase of only one system while achieving multiple functions, and also thereby reduces the amount of equipment needed in an operating room, thus reducing clutter and allowing space for other necessary equipment.

SUMMARY OF THE INVENTION

A system includes a surgical gas delivery device with a filter cartridge interface and a computer controlled control unit configured to control the circulation of surgical gas during endoscopic surgery. The control unit is configured to operate in a plurality of different modes of operation. A tube set assembly includes a tube set for connecting the surgical gas delivery device to one or more end effectors and includes a filter cartridge in fluid communication with the tube set. The filter cartridge is seated in the filter cartridge interface of the surgical gas delivery device to communicate surgical gas between the surgical gas delivery device and the one or more end effectors. The filter cartridge includes a data carrying element. The surgical gas delivery device includes a reader operatively connected to receive input from the data carrying element. The control unit is operatively connected to the reader to receive input from the data carrying element indicative of which one of the plurality of different modes of operation to use in controlling the circulation of surgical gas during a surgical procedure.

The data carrying element, the reader, and the control unit can be configured to launch a specific one of the plurality of different modes of operation when the filter cartridge is inserted into the filter cartridge interface. It is also contemplated that the data carrying element, the reader, and the control unit can be configured to receive user input indicative of a desired mode of operation of the plurality of different modes of operation, to prompt the user to insert a filter cartridge compatible with the desired mode of operation into the filter cartridge interface, and to launch the desired mode of operation for the surgical gas delivery device only if the data carrying element of the filter cartridge seated in the filter cartridge interface matches the desired mode of operation.

The plurality of different modes of operation can include a first mode involving recirculation of surgical gas and insufflation of a surgical cavity and a second mode involving smoke evacuation from a surgical cavity. The plurality of different modes of operation can include a third mode involving only insufflation of a surgical cavity and/or a fourth mode that is a sub-mode involving recirculation of surgical gas and insufflation of a surgical cavity, or a mode for vacuum suction in open surgery. The data carrying element of the filter cartridge can include machine readable information that causes the control unit to operate the surgical gas delivery device in one and only one of the modes in the plurality of different modes of operation, e.g., the machine readable information can be configured to launch a specific one of the plurality of different modes of operation when the filter cartridge is inserted into the filter cartridge interface.

The data carrying element can be wirelessly connected to the reader. The data carrying element can include at least one of a radio-frequency identification (RFID) transponder, a bar code, and/or a near-field communication (NFC) chip. The reader can includes at least one of an RFID reader, a bar code reader, and/or an NFC reader. The data carrying element can include machine readable information configured to cause the control unit to operate the surgical gas delivery device or to refuse to operate the surgical gas delivery device based on at least one of: whether the filter cartridge is authentic, whether the filter cartridge has previously been used, whether the filter cartridge still has allowable uses remaining wherein the tube set is reusable, whether any applicable calibration data is within an acceptable range, and/or whether the filter cartridge has passed its expiration date. The reader can be part of a reader/writer device that includes a writer configured to write data from the surgical gas delivery device to the data carrying element of the filter cartridge. The writer can write onto the data carrying element that the tube set was used, or mark a usage, for example.

A filtered tube set assembly for a system as described above can include a single lumen tube set in fluid communication with the filter cartridge, wherein the machine readable information of the data carrying element is configured to cause the control unit to operate in a mode involving only insufflation. It is also contemplated that a tube set assembly can include a tri-lumen tube set in fluid communication with the filter cartridge, wherein the machine readable information of the data carrying element is configured to cause the control unit to operate in a mode involving recirculation and insufflation. In another aspect, a tube set assembly can include a dual-lumen tube set in fluid communication with the filter cartridge, wherein the machine readable information of the data carrying element is configured to cause the control unit to operate in a mode involving smoke evacuation. It is also contemplated that the tube set assembly can have a configuration involving recirculation of surgical gas and insufflation of a surgical cavity, and the machine readable information of the data carrying element can be configured to cause the control unit to launch a mode involving recirculation of surgical gas and insufflation of the surgical cavity.

A method of supplying surgical gas from a surgical gas delivery device includes receiving a filter cartridge in a filter cartridge interface of the surgical gas delivery device. The method includes reading machine readable information from a data carrying element of the filter cartridge, and automatically launching one of a plurality of different modes of operation based on the machine readable information from a data carrying element.

The method can include displaying a prompt on a user interface for a user to select the one mode of operation from among the plurality of different modes of operation, receiving user input indicative of the one mode of operation, and prompting the user with the user interface to insert a filter cartridge compatible with the one mode of operation into the filter cartridge receptacle, wherein launching the one mode of operation includes launching the one mode only upon insertion of the filter cartridge compatible with the one mode of operation into the filter cartridge interface. In another aspect, the method can include launching the one mode of operation directly upon insertion of a filter cartridge compatible with the one mode of operation without the user entering input on a user interface to select the one mode of operation.

The method can include prompting a user to select a sub-mode of the one mode of operation and receiving user input indicative of the sub-mode, wherein launching the one mode of operation includes launching the sub-mode of the one mode of operation. The method can include updating a remote database to track when the data carrying element is read in the surgical gas delivery device. The method can include writing data from the surgical gas delivery device to the data carrying element of the filter cartridge.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
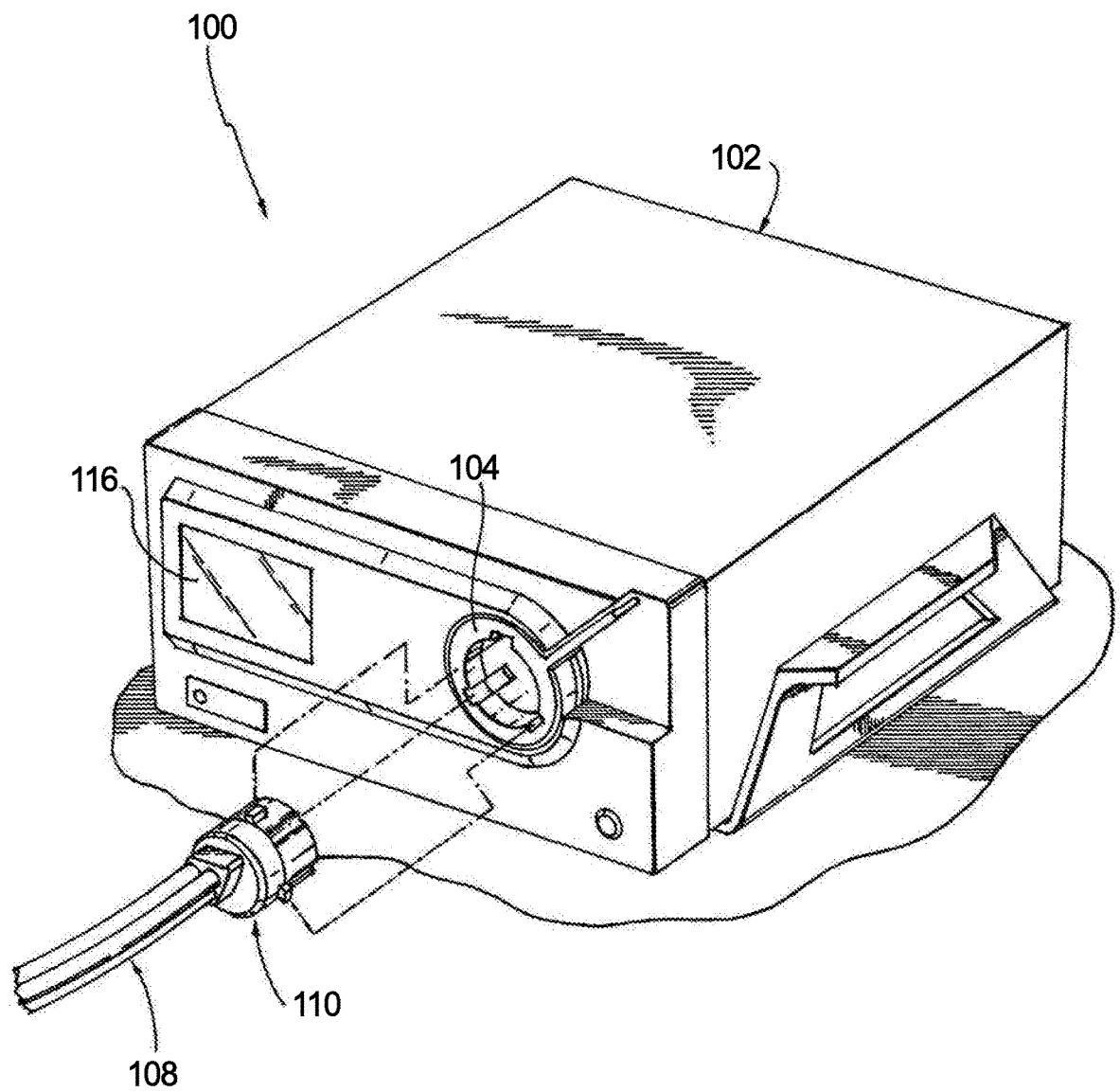
FIG. 1 is an exploded perspective view of an exemplary embodiment of a system constructed in accordance with the present disclosure, showing the surgical gas delivery device and a tube set with a filter cartridge.

Reference will now be made to the drawings wherein like reference numerals identify similar structural features or aspects of the subject disclosure. For purposes of explanation and illustration, and not limitation, a partial view of an exemplary embodiment of a system in accordance with the disclosure is shown in FIG. 1 and is designated generally by reference character 100. Other embodiments of systems in accordance with the disclosure, or aspects thereof, are provided in FIGS. 2-8, as will be described.

Figure 3:
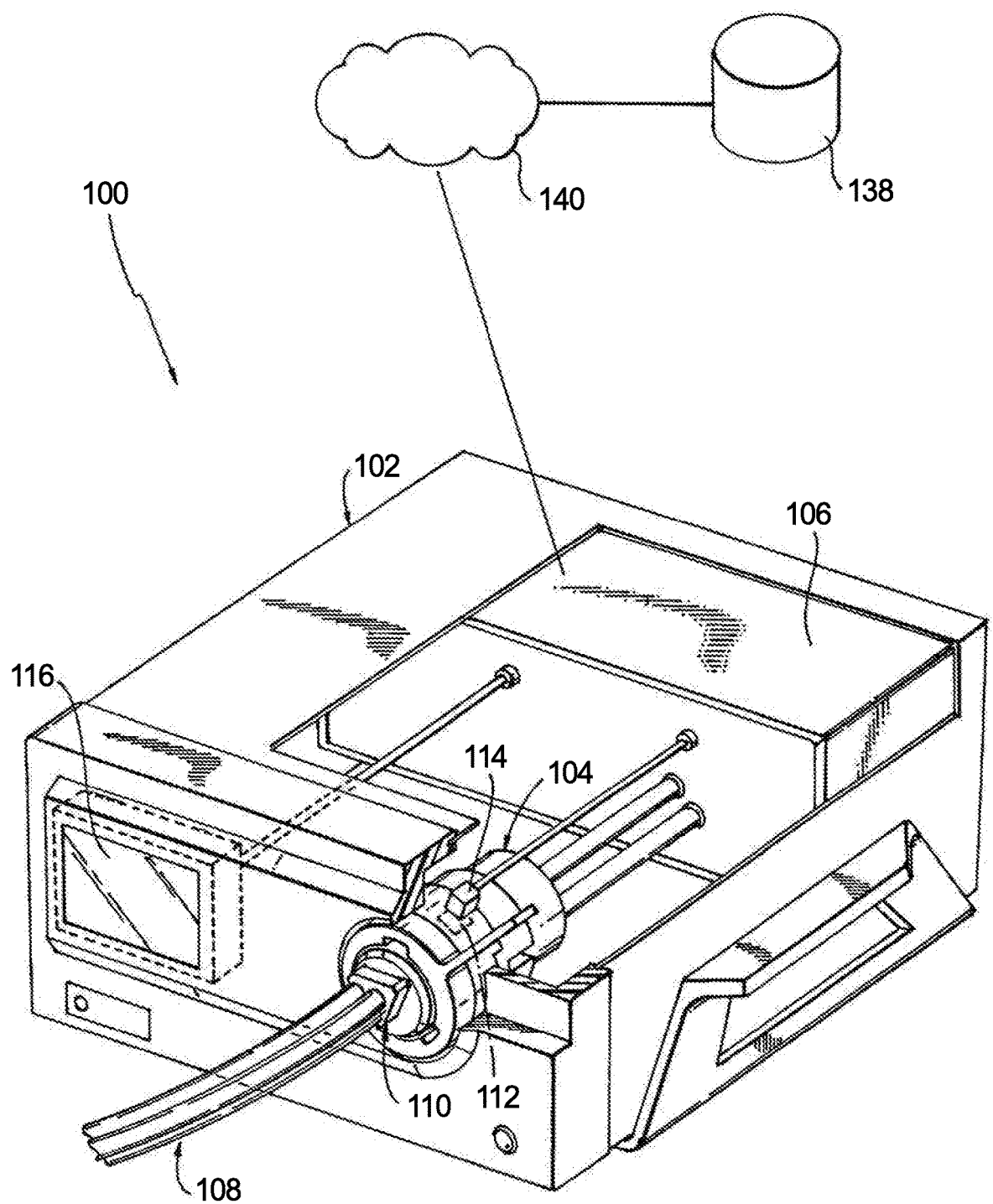
FIG. 3 is a schematic view of the surgical gas delivery device of FIG. 1, showing the computer controlled control unit.

The system 100 includes a surgical gas delivery device 102 with a filter cartridge interface 104 and a computer controlled control unit 106, shown in FIG. 3, configured to control the circulation of surgical gas during endoscopic surgery. The control unit 106 can operate the surgical gas delivery device 102 in a plurality of different modes of operation. A tube set assembly 107 includes a tube set 108 for connecting the surgical gas delivery device 102 to one or more end effectors or access devices such as trocars. A filter cartridge 110 is in fluid communication with the tube set 108.

Figure 2:
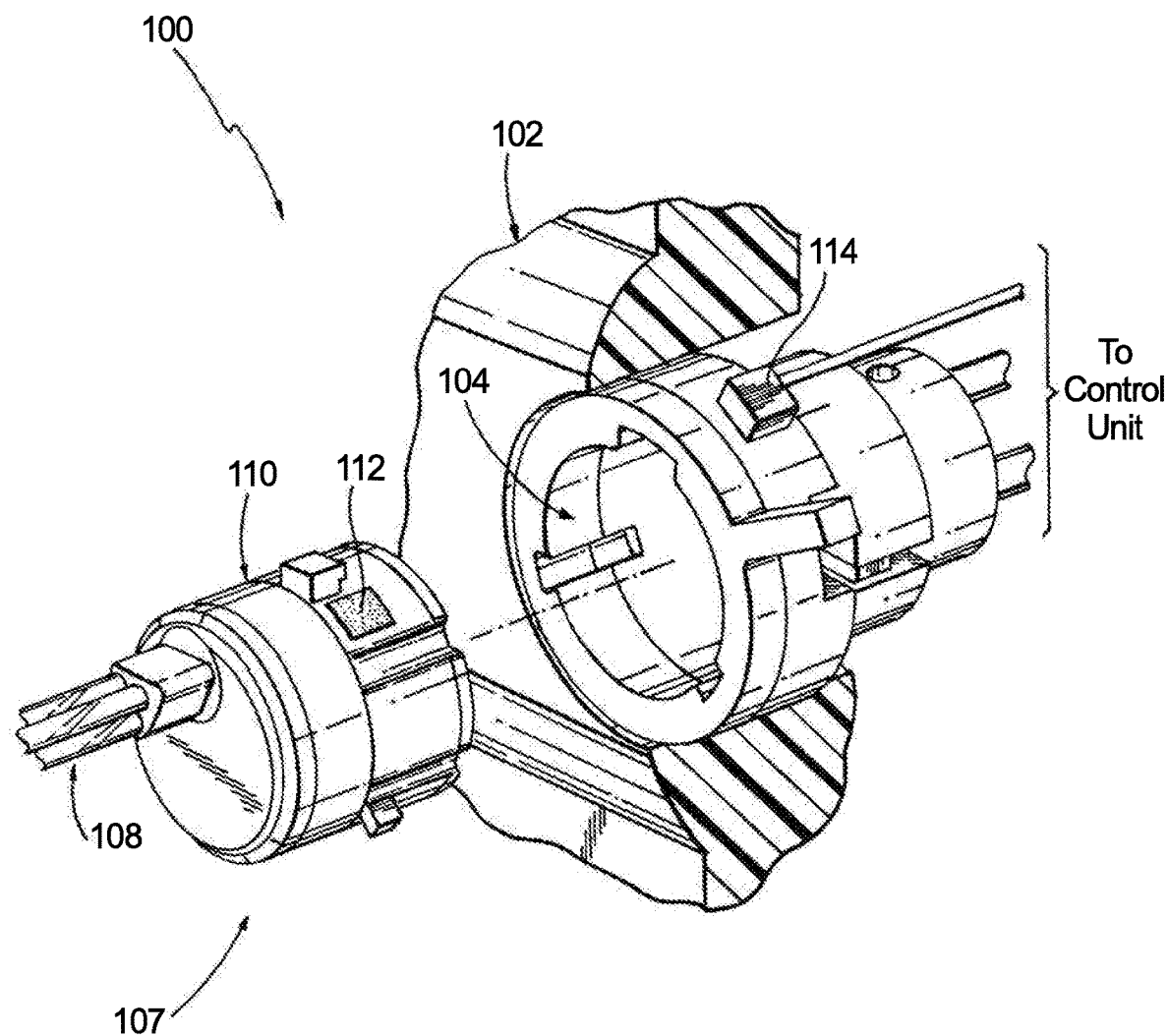
FIG. 2 is a partially cut-away exploded perspective view of a portion of the system of FIG. 1, showing the data carrying element of the filter cartridge and the reader of the surgical gas delivery device.

With reference now to FIG. 2, the filter cartridge 110 can be seated in the filter cartridge interface 104 of the surgical gas delivery device 102 to communicate surgical gas between the surgical gas delivery device 102 and the one or more access devices, e.g., at the opposite end of the tube set 108 from the filter cartridge 110. The filter cartridge 110 includes a data carrying element 112. The surgical gas delivery device 102 includes a reader 114, which is depicted as being integrated in the filter cartridge interface 104. Those skilled in the art will readily appreciate that the reader 114 can be situated in any other suitable location in system 100 without departing from the scope of the present disclosure. Those skilled in the art will also readily appreciate that the placement of data carrying element 112 can be situated in any other suitable location such that it can readily interface with reader 114 without departing from the scope of the present disclosure.

With reference now to FIG. 3, the reader 114 is operatively connected to receive input from the data carrying element 112. Different types of data carrying elements 112 and readers 114 (e.g., RFID, NFC, or the like as described below) can connect wirelessly for the reader 114 to read the data of the data carrying element 112. Different RFID tags, for example, have varying distances over which they can be read. The operative connection between the reader 114 and the data carrying element 112 includes physical proximity, as well as absence of any inhibiting or blocking materials (such as signal-blocking metals) in the pathway between the data carrying element 112 and the reader 114. The control unit 106 is operatively connected to the reader 114 to receive input from the data carrying element 112 indicative of which one of the plurality of different modes of operation to use in controlling the circulation of surgical gas during a surgical procedure. A user interface 116 is connected to the control unit 106 for displaying prompts to a user, and for accepting input from a user, such as in a touch screen interface device, for example.

The data carrying element 112 of filter cartridge 110, the reader 114, and the control unit 106 are configured to launch a specific one of the plurality of different modes of operation when the filter cartridge 110 is inserted into the filter cartridge interface 104, e.g., without requiring any other input from the user to launch the correct mode. It is also contemplated that the filter cartridge 110, the reader 114, and the control unit 106 can be configured to receive user input indicative of one mode, e.g., a desired mode, of operation of the plurality of different modes of operation, e.g. using the user interface 116 to prompt the user to insert a filter cartridge compatible with the desired mode of operation into the filter cartridge interface 104. In this case, the control unit 106 launches the desired mode of operation for the surgical gas delivery device only if the data carrying element 112 of the filter cartridge 110 seated in the filter cartridge interface 104 matches the desired mode of operation.

Figure 4:
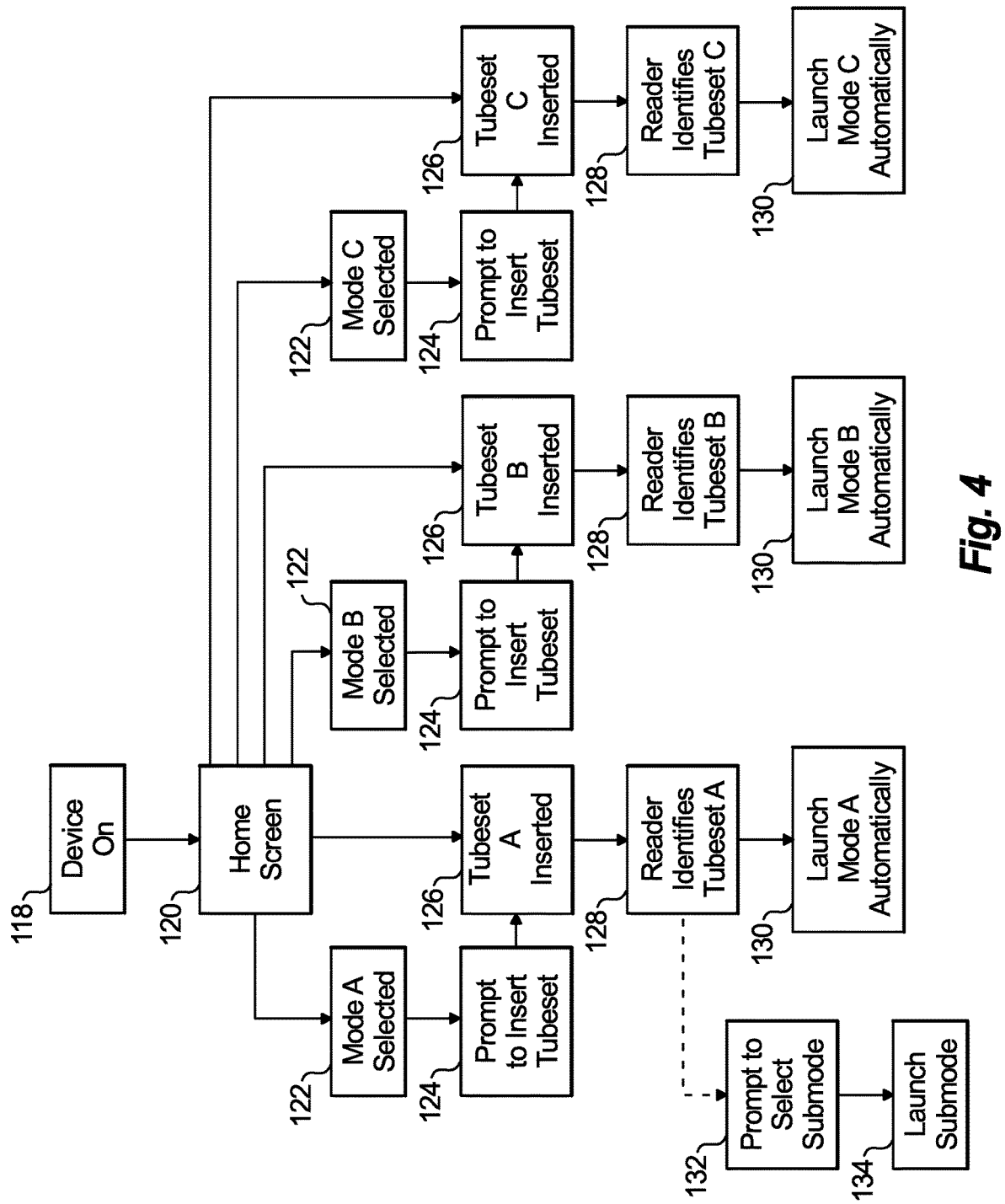
FIG. 4 is a flow diagram of mode selection operations for the surgical gas delivery device of FIG. 1, showing methods of automatic launching different modes of operation.

With reference now to FIG. 4, a flow diagram for an exemplary embodiment is shown in which there are three modes of operation, one of which has a sub-mode option. At box 118, gas delivery device 102 is powered on, including powering control unit 106. At box 120, user interface 116 displays a home screen, which can display a prompt for a user to select the desired mode of operation, e.g. mode A, mode B, or mode C, from among the plurality of different modes of operation, e.g., modes A, B, and C. The user interface 116 receives user input indicative of the desired mode of operation and prompts the user to insert a filter cartridge compatible with the desired mode of operation into the filter cartridge receptacle 104. For example, if the user selects mode A as indicated in box 122 the user interface 116 prompts the user to insert a corresponding tube set into the filter cartridge interface 104, as indicated in Box 124. It is also contemplated that, at box 120, the user interface 116 could display a home screen which prompts the user to insert a tube set to begin mode selection.

The data carrying element 112 of the filter cartridge 110 includes machine readable information that causes the control unit 106 to operate the surgical gas delivery device in one of the modes of operation. This can mean the control unit will operate in one and only one of the modes in the plurality of different modes of operation so that only the correct mode of operation is used for the tube set inserted into the filter cartridge interface 104. Each mode of operation may potentially include sub-modes of operation as explained below. So for example, if the user inserts the proper tube set for mode A into the filter cartridge receptacle 116, as indicated with box 126, the reader 114 will provide input to the control unit 106 from the machine readable information of the data carrying element 112, which will identify the fact that a proper tube set for mode A is seated in filter cartridge interface 104, as indicated with box 128. Then the control unit 106 will launch mode A automatically as indicated in box 130, to begin supplying surgical gas using the mode of operation associate with mode A. If the tube set inserted does not correspond to the user-selected mode, the user interface 116 can display a prompt alerting the user of the error.

It is also possible to circumvent the user selection and prompting of boxes 122 and 124, i.e., to launch the desired mode of operation directly upon insertion of a filter cartridge 110 compatible with the desired mode of operation. For example, from the home screen at box 120, a user can insert a tube set for mode A into the filter cartridge interface 104. The reader 114 and control unit 106 will identify the tube set as being for mode A based on the machine readable information in the data carrying element 112. Then, without any input or prompts at user interface 116, the control unit 106 can automatically launch mode A. Modes B and C have similar operation boxes 122, 124, 126, 128, and 130 to those described above for launching mode A. With the mode launched, the user interface 116 can display a prompt telling the user which mode was launched.

With continued reference to FIG. 4, one or more of the modes of operation can include one or more sub-modes, as indicated by the ellipses in FIG. 4. If a mode of operation is selected, either through user input to the user interface 116, or by simply inserting a filter cartridge into the filter cartridge interface 104, where the mode of operation includes optional sub-modes, the user interface 116 can prompt the user to select which sub-mode is desired at box 132. Once the user indicates the desired sub-mode through input to the user interface 116 (and once the filter cartridge from an appropriate tube set is inserted in the filter cartridge interface 104), the control unit 106 can launch the specified mode of operation in the desired sub-mode as indicated by box 134. This would be useful, for example, in differentiating between the use of the tube sets shown in FIGS. 7 and 8, which are described below.

Figure 5:
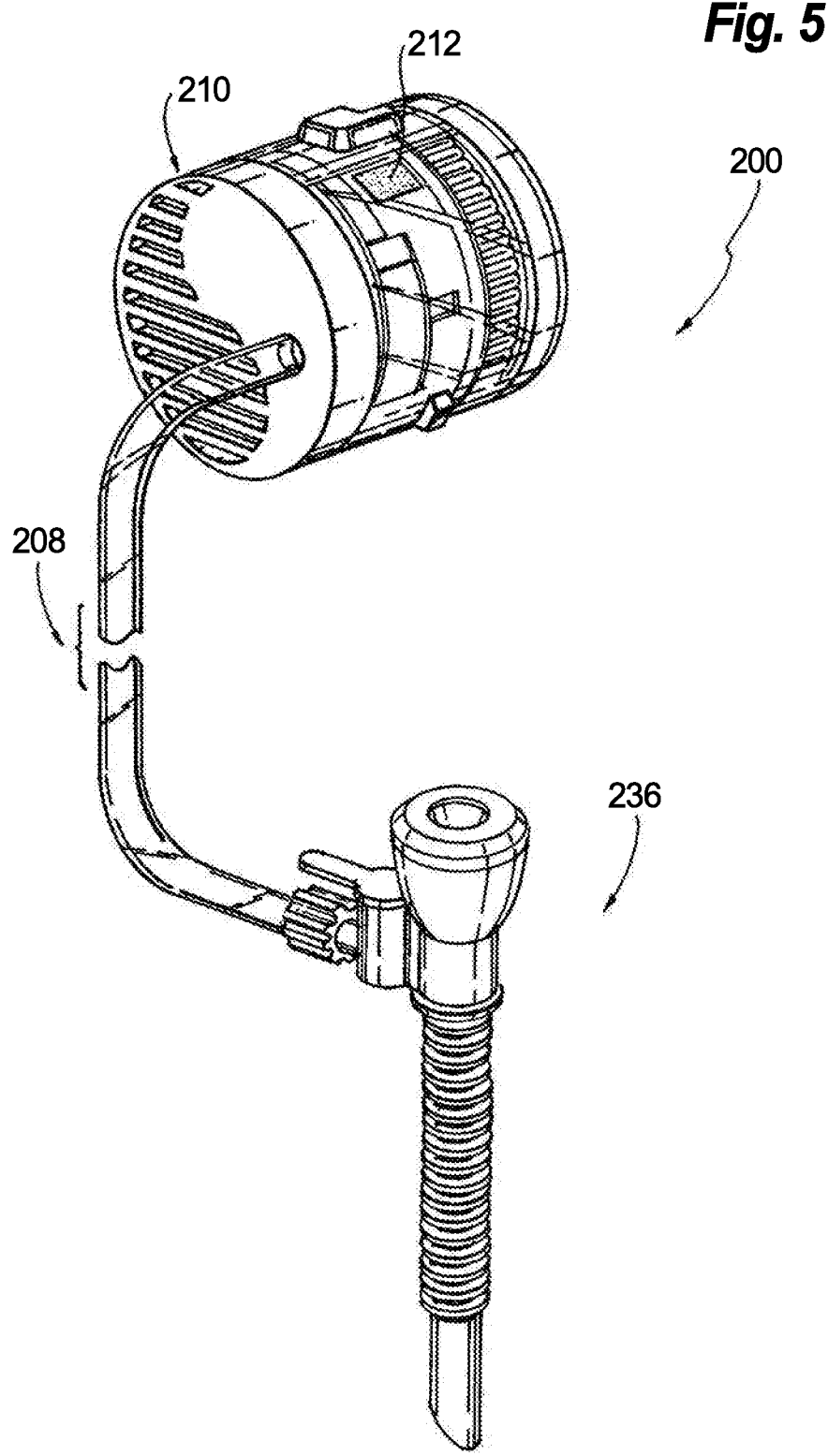
FIG. 5 is a perspective view of an exemplary embodiment of a tube set for use with the gas delivery system of FIG. 1, showing a single lumen configuration for an insufflation only mode.

With reference now to FIG. 5, a tube set assembly 200 is shown for a system 100 as described above. The tube set 208 of the tube set assembly 200 includes a single lumen in fluid communication with the filter cartridge 210 on one end, and on the other end with a trocar 236 for insufflation. The machine readable information of the data carrying element 212 is configured to cause the control unit 106 to operate in a mode of operation involving only insufflation of a surgical cavity, e.g., to launch the system into an insufflation only mode. For example, the single lumen of tube set 208 can be used for insufflation and pressure sensing in one sub-mode, or as a vacuum for open surgery in a second sub-mode. It is also contemplated that these two distinct functionalities could be differentiated via the programming of the data carrying element 212 and could cause the control unit 106 to launch either an insufflation and pressure sensing mode or a vacuum for open surgery mode depending on the data in data carrying element 212, for example.

Figure 6:
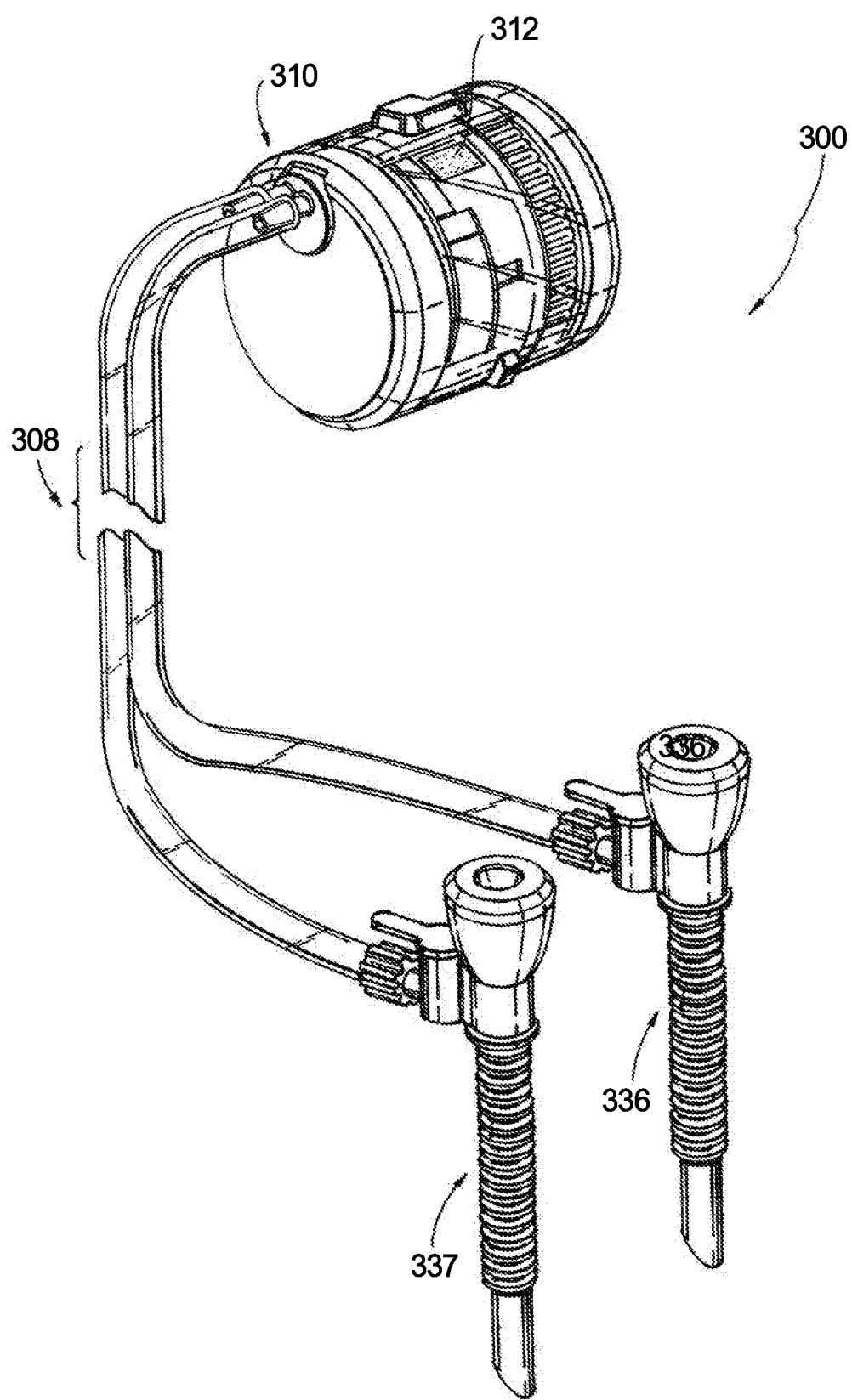
FIG. 6 is a perspective view of an exemplary embodiment of a tube set for use with the gas delivery system of FIG. 1, showing a dual lumen configuration for a smoke evacuation mode.

Referring now to FIG. 6, a tube set assembly 300 is shown that can be used with the system 100 as described above. The tube set assembly 300 includes a bifurcated dual-lumen tube set 308 in fluid communication with the filter cartridge 310 on one end and with trocar 336 and 337 on the respective bifurcated ends for smoke evacuation from a body cavity. The machine readable information of the data carrying element 312 is configured to cause the control unit 106 to operate in a mode involving smoke evacuation, e.g., to launch the system 100 into a smoke evacuation mode. One of the two lumens of tube set 308 can be a positive pressure line for supplying gas for smoke evacuation, and the other line can be a negative pressure or vacuum line for removing smoke evacuation gas from the patient.

Figure 7:
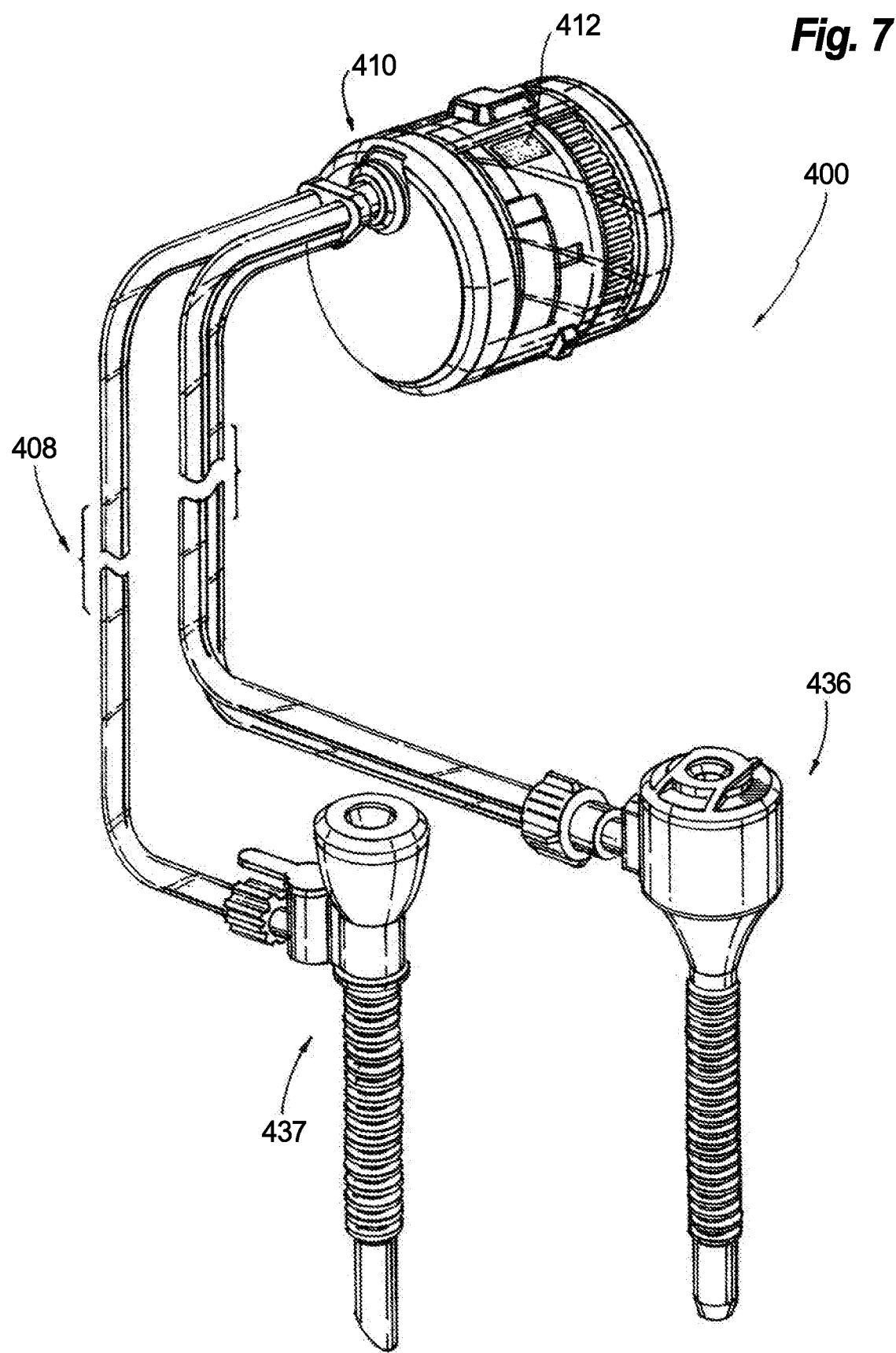
FIG. 7 is a perspective view of an exemplary embodiment of a tube set for use with the gas delivery system of FIG. 1, showing a tri-lumen configuration for a recirculation and insufflation mode.

With reference to FIG. 7, a tube set assembly 400 is shown that can be used with the system 100 as described above. The tube set assembly 400 includes a tri-lumen tube set 408 in fluid communication with the filter cartridge 410 at one end and at the other end with one trocar 436 attached to the high pressure recirculation gas supply and the vacuum recirculation gas return. Another trocar 437 is a separate standard trocar attached to the insufflation/pressure sense line. Trocars 436 and 437 provide for recirculation of surgical gas and insufflation of a surgical cavity. The machine readable information of the data carrying element 412 is configured to cause the control unit 106 to operate in a mode involving recirculation and insufflation, e.g., to launch the system 100 into a recirculation and insufflation mode. For example, a tri-lumen tube set 408 can be configured to have one lumen for high pressure recirculation gas supply, one line for negative pressure or vacuum recirculation gas return, and one line for insufflation and pressure sensing. This tube set/mode could operate a gas-sealed valveless access port such as the one disclosed in U.S. Pat. No. 8,795,223. It is also contemplated that a tri-lumen tube set 408 can be bifurcated to have the insufflation and sensing line spaced apart from the other two lumens at the access device end of the tube set 408.

Figure 8:
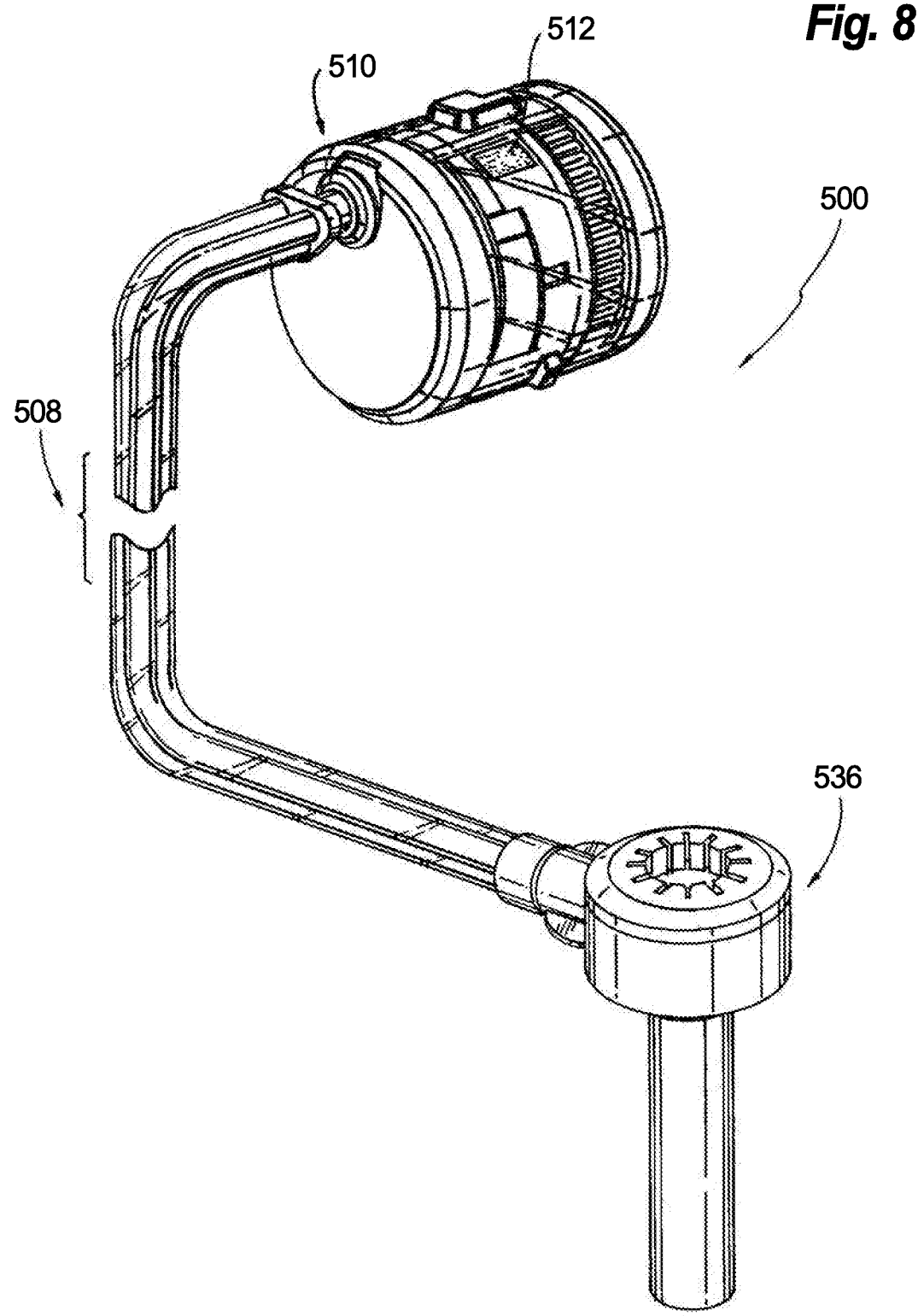
FIG. 8 is a perspective view of an exemplary embodiment of a tube set for use with the gas delivery system of FIG. 1, showing a tri-lumen configuration for a single pneumatically sealed trocar.

With reference now to FIG. 8, another example of a tri-lumen tube set assembly 500 is shown that can be used with the system 100 as described above. The tube set assembly 500 includes a tri-lumen tube set 508 in fluid communication with the filter cartridge 510 at one end and at the other end with a single trocar 536 for recirculation of surgical gas and insufflation of a surgical cavity from the single trocar 536. The machine readable information on the data carrying element 512 is configured to cause the control unit 106 to operate in a mode involving recirculation and insufflation, e.g., to launch the system 100 in to a recirculation and insufflation mode. For example, a tri-lumen tube set 508 can be configured to have one lumen for high pressure recirculation gas supply, one line for negative pressure or vacuum recirculation gas return, and one line for insufflation and pressure sensing.

The data carrying elements 112, 212, 312, 412, and 512 can be wirelessly connected to the reader 114 of FIGS. 2-3. The data carrying elements 112, 212, 312, 412, and 512 can each include a radio-frequency identification (RFID) transponder, a bar code, and/or a near-field communication (NFC) chip. The reader 114 can correspondingly include an RFID reader, a bar code reader, and/or an NFC reader. The data carrying elements 112, 212, 312, 412, and 512 can be included on or in the filter cartridge 110, 210, 310, 410, and 510 in any suitable manner, including as a sticker adhered to an exterior surface of the filter cartridge, inserted into an available chamber, or injection molded into the body of the filter cartridge, for example.

In addition to determining the launch mode, the data carrying elements 112, 212, 312, 412, and 512 can include machine readable information configured to cause the control unit 106 to operate the surgical gas delivery device 102 or to refuse to operate the surgical gas delivery device 102 based on at least one of: whether the filter cartridge is authentic, whether the filter cartridge has previously been used, whether the filter cartridge still has allowable uses remaining wherein the tube set is reusable, whether any applicable calibration data is within an acceptable range, and/or whether the filter cartridge has passed its expiration date.

It is also contemplated that the reader 114 of FIGS. 2-3 can be part of a reader/writer device that includes a writer configured to write data from the surgical gas delivery device 102 to the data carrying element 112, 212, 312, 412, and 512 of the filter cartridge 110, 210, 310, 410, or 510. RFID tags, for example, can be written with permanent and re-writeable data. For example, after using a tube set 108, the reader 114 with a writer could write onto a tag, e.g., data carrying element 112, data indicating that the tube set 108 has been used and this will be permanent and will prevent the tube set 108 from being used in any other device. In another example involving reusable tubesets, the reader 114 can include a writer that writes data to the data carrying element 112, 212, 312, 412, and 512 to increment a count of how many times the filter cartridge has been used. If the count exceeds a set limit, then the control unit 106 can refuse to launch the associated mode of operation the next time the filter cartridge is inserted into the filter cartridge interface 104. Other information that can be written to the data carrying element 112, 212, 312, 412, and 512 include a usage time/date which could be helpful for servicing or tracking user feedback, for example. With or without the reader 114 also including a writer, system 100 can update a remote database 138, e.g., connected to the control unit 106 through a cloud or network 140 as shown in FIG. 2, to track when the data carrying element 112, 212, 312, 412, and 512 is read in the surgical gas delivery device.

Systems and methods as disclosed herein provide advantages from using the data carrying element to drive mode launch. This enables simpler scalability of product development relative to traditional mode launching, and ensures compatibility with the software system of the multimodal insufflation system. For example, implementing methods as disclosed herein can ensure that when a new tube set product and/or mode is developed, it cannot be used with an incorrect control system because it will require a reader to be programmed to recognize the new tube set product and/or mode and to launch a mode designed to accept that specific new tube set product and/or mode.

The methods and systems of the present disclosure, as described above and shown in the drawings, provide for surgical gas delivery with superior properties including ease of use. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A system comprising:
a surgical gas delivery device including a filter cartridge interface and a computer controlled control unit configured to control circulation of surgical gas during an endoscopic surgery, wherein the control unit is configured to operate in a plurality of different modes of operation; and
a tube set assembly including a tube set for connecting the surgical gas delivery device to one or more end effectors and including a filter cartridge in fluid communication with the tube set, the filter cartridge being seated in the filter cartridge interface of the surgical gas delivery device to communicate surgical gas between the surgical gas delivery device and the one or more end effectors, wherein the filter cartridge includes a data carrying element, and wherein the surgical gas delivery device includes a reader operatively connected to receive input from the data carrying element, wherein the control unit is operatively connected to the reader to receive input from the data carrying element indicative of which one of the plurality of different modes of operation to use in controlling circulation of surgical gas during the endoscopic surgery, wherein the data carrying element is wirelessly connected to the reader, wherein the data carrying element, the reader, and the control unit are configured to automatically launch a specific one of the plurality of different modes of operation when the filter cartridge is inserted into the filter cartridge interface based on machine readable information in the data carrying element without any user input, wherein the plurality of different modes of operation includes at least one of:
a first mode involving recirculation of surgical gas and insufflation of a surgical cavity;
a second mode involving smoke evacuation from a surgical cavity;
a third mode involving only insufflation of a surgical cavity; or
a fourth mode for vacuum suction in open surgery.

2. The system as recited in claim 1, wherein the data carrying element of the filter cartridge includes machine readable information that causes the control unit to operate the surgical gas delivery device in one and only one of the modes in the plurality of different modes of operation.

3. The system as recited in claim 1, wherein the data carrying element includes at least one of a radio-frequency identification (RFID) transponder, a bar code, and/or a near-field communication (NFC) chip.

4. The system as recited in claim 3, wherein the reader includes at least one of an RFID reader, a bar code reader, and/or an NFC reader.

5. The system as recited in claim 1, wherein the data carrying element includes machine readable information configured to cause the control unit to operate the surgical gas delivery device or to refuse to operate the surgical gas delivery device based on at least one of: whether the filter cartridge is authentic, whether the filter cartridge has previously been used, whether the filter cartridge still has allowable uses remaining wherein the tube set is reusable, whether any applicable calibration data is within an acceptable range, and/or whether the filter cartridge has passed its expiration date.

6. The system as recited in claim 1, wherein the reader is part of a reader/writer device that includes a writer configured to write data from the surgical gas delivery device to the data carrying element of the filter cartridge.

7. A filtered tube set assembly comprising:
a tube set for connecting a surgical gas delivery device to one or more end effectors and including a filter cartridge in fluid communication with the tube set, wherein the filter cartridge is configured to be seated in a filter cartridge interface of the surgical gas delivery device to communicate surgical gas between the surgical gas delivery device and the one or more end effectors, and wherein the filter cartridge includes a data carrying element configured to connect with a reader of the surgical gas delivery device to provide input to a control unit of the surgical gas delivery device, wherein the data carrying element includes machine readable information configured to cause the control unit to operate in a specific one of a plurality of different modes of operation to use in controlling circulation of surgical gas during a surgical procedure, wherein the data carrying element is configured to be wirelessly connected to the reader, wherein the data carrying element, the reader, and the control unit are configured to automatically launch a specific one of the plurality of different modes of operation when the filter cartridge is inserted into the filter cartridge interface based on machine readable information in the data carrying element without any user input, wherein the plurality of different modes of operation includes at least one of:
- a first mode involving recirculation of surgical gas and insufflation of a surgical cavity;
- a second mode involving smoke evacuation from a surgical cavity;
- a third mode involving only insufflation of a surgical cavity; or
- a fourth mode for vacuum suction in open surgery.

8. The tube set assembly as recited in claim 7, wherein the data carrying element of the filter cartridge includes machine readable information that causes the control unit to operate the surgical gas delivery device in one and only one of the modes in the plurality of different modes of operation.

9. The tube set assembly as recited in claim 7, wherein the data carrying element includes at least one of a radio-frequency identification (RFID) transponder, a bar code, and/or a near-field communication (NFC) chip.

10. The tube set assembly as recited in claim 7, wherein the data carrying element includes machine readable information configured to cause the control unit to operate the surgical gas delivery device or to refuse to operate the surgical gas delivery device based on at least one of: whether the filter cartridge is authentic, whether the filter cartridge has previously been used, whether the filter cartridge still has allowable uses remaining wherein the tube set is reusable, whether any applicable calibration data is within an acceptable range, and/or whether the filter cartridge has passed its expiration date.

11. The tube set assembly as recited in claim 7, further comprising a single lumen tube set in fluid communication with the filter cartridge, wherein the machine readable information of the data carrying element is configured to cause the control unit to operate in one of a mode involving only insufflation or a mode involving vacuum suction for open surgery.

12. The tube set assembly as recited in claim 7, further comprising a tri-lumen tube set in fluid communication with the filter cartridge, wherein the machine readable information of the data carrying element is configured to cause the control unit to operate in a mode involving recirculation and insufflation.

13. The tube set assembly as recited in claim 7, further comprising a dual-lumen tube set in fluid communication with the filter cartridge, wherein the machine readable information of the data carrying element is configured to cause the control unit to operate in a mode involving smoke evacuation.

* * * * *